United States Patent [19]

Cierpka

[11] Patent Number: 4,822,784
[45] Date of Patent: Apr. 18, 1989

[54] COMPLEX SALT

[76] Inventor: Henning Cierpka, Stockackerstrasse 1 a, 4153 Reinach, Switzerland

[21] Appl. No.: 861,853

[22] Filed: May 12, 1986

Related U.S. Application Data

[60] Division of Ser. No. 633,243, Jul. 23, 1984, Pat. No. 4,721,707, which is a continuation-in-part of Ser. No. 456,128, Jan. 6, 1983, Pat. No. 4,740,506.

[30] Foreign Application Priority Data

Jan. 22, 1982 [CH] Switzerland ............................ 388/82
Jan. 22, 1982 [CH] Switzerland ............................ 389/82

[51] Int. Cl.$^4$ ............................................ A61K 31/555
[52] U.S. Cl. .................................................. 514/184
[58] Field of Search ........................................ 514/184

[56] References Cited

PUBLICATIONS

MacRae et al., "Anaesthesia"—vol. 36, pp. 312–315 (1981).

Primary Examiner—Stanley J. Friedman
Attorney, Agent, or Firm—Sandler & Greenblum

[57] ABSTRACT

A composition comprising a nitroprusside of a short acting ganglionic blocking agent selected from the group consisting of sulfonium salts and ammonium salts.

4 Claims, 4 Drawing Sheets

COMPLEX SALT

CONTINUATION-IN-PART STATUS

This Application is a divisional of Ser. No. 633,243, filed July 23, 1984, now U.S. Pat. No. 4,721,707, which is a Continuation-in-Part of Ser. No. 456,128 filed Jan. 6, 1983, now U.S Pat. No. 4,740,506 the disclosures of which are incorporated by reference thereto.

BACKGROUND OF THE INVENTION

1. Field of the Invention

The invention relates to novel nitroprussides of shortacting ganglionic blocking agents, particularly to the novel compound bis-(trimethaphan)-nitroprusside and its (+)-isomer of formula

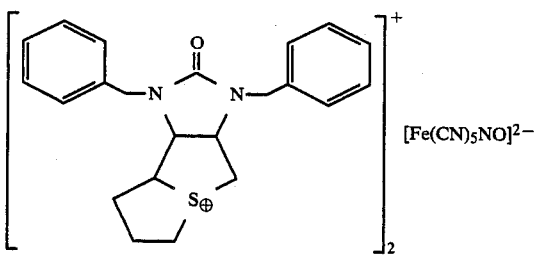

and solvates, especially hydrates or alcoholates thereof, as well as a process for the manufacture thereof from an alkali nitroprusside and a soluble trimethaphan salt, especially sodium nitroprusside and trimethaphan camsylate, in solution, especially in water.

The invention also relates to mixtures of an alkali metal nitroprusside, such as sodium nitroprusside, and a soluble salt of a short acting ganglionic agent, such as a soluble trimethaphan salt, particularly of (+)-trimethaphan. Trimethaphan camsylate or halogenide, such as the chloride or bromide, are also suitable.

The invention further relates to concentrated solutions (stock solutions) containing said novel nitroprussides and mixtures.

Furthermore, the invention relates to pharmaceutical compositions which contain said novel nitroprussides and mixtures in solid form, in form of concentrated solutions or in form of diluted solutions suitable for infusion purposes.

Preferred mixtures described are those containing the nitroprusside and the salt of a short acting ganglionic blocking agent, especially of trimethaphan or its (+)-isomer, in the weight ratio of 1:<10, especially in a ratio representing the nitroprusside salt of the ganglionic blocking agent, e.g., bis-(trimethaphan)-nitroprusside. Also described are solutions, especially concentrated (stock) solutions of said nitroprussides and mixtures in physiologically acceptable alcohols, especially in aqueous ethanol.

Also described are said nitroprussides, especially bis-(trimethaphan)-nitroprusside, as well as its solvates, and said mixtures, especially those of an alkali nitroprusside and a soluble trimethaphan salt, preferably in the weight ratio of less than 1:10, especially of about 1:4, when being dissolved in a physiologically acceptable alcohol, especially in aqueous ethanol, especially at least 40% or preferably about 60% ethanol.

As was noted above, the invention relates to the use of the inventive composition in a weight ratio of less than 1:10, and preferably about 1:4. The invention thus includes the range of 1:4—<10. Within this range, narrower ranges of 1:9, 1:8, 1:7, 1:6, and 1:5 may be listed by way of example. It is clear, of course, that although integers are listed, intermediate ranges are also possible within the range set forth above.

Preferably, these nitroprussides and mixtures are stored in the solid form and dissolved in said alcohol immediately before use. In such a case the alcohol may, in addition, contain other physiologically acceptable alcohols, such as polyols, like glycerol, inositol, pentaerythritol, mannitol or isosorbitol as well as nitrates, like mono-, di-, tri- or tetranitrates, thereof, especially nitroglycerin, preferably in an amount not exceeding the amount of nitroprusside to be dissolved, as well as nucleosides, such as inosine and adenosine, short acting positive inotropic agents, such as dopamine or dobutamine, a physiologically acceptable thiosulfate, such as sodium thiosulfate, or nicotinic acid and/or its biological precursors, like beta-pyridylcarbinol.

The invention further relates to preparation of infusion solutions from the concentrated solutions or mixtures, the preparation of an especially well soluble micronized mixture of (I) and thiosulphate or of the mixture of the salts and thiosulphate, and the use of the concentrate for the preparation of infusion solutions.

The compound (I), its solvates, the mixture of the salts, and the pharmaceutical compositions containing (I) or the mixture of the salts, are suitable for therapeutic use, particularly in the lowering of blood pressure, in the achievement of peripheral vasodilation, in the elimination of arterial spasms and/or in the reduction of myocardial oxygen consumption and of the work load of the heart after heart attack.

2. Description of the Prior Art

Sodium nitroprusside is a known infusion preparation for the rapid and controlled lowering of the blood pressure in the case of operations or hypertensive crises and for reducing the work load of the heart, e.g., in the case of heart attack. However, it has disadvantages which restrict the use of this valuable and extraordinarily well controllable medicament. Thus, it decomposes in the body very rapidly with the formation of up to 5 moles of cyanide per molecule. Since cyanide is an acutely toxic agent which blocks the respiratory chain and paralyses the respiratory center, SNP must be used in order to avoid an accumulation of toxic cyanide concentrations in the blood serum only with the strictest maintenance of prescribed highest dosages and even then only for a short time.

In common with other vasodilators SNP has the disadvantage that the desired rapid and powerful lowering of blood pressure leads very frequently to an activation of the so-called counter-regulation, whereby, in turn, the amount of circulating hormones which increase blood pressure (adrenalin, noradrenalin and angiotensin II) and of renin is greatly increased. This causes, especially in young patients, a strong tendency to increased blood pressure which can be compensated only by successive increase of the dosage of SNP to be infused (tachyphylaxis). If in such cases the administration of SNP is not discontinued, a dangerous increase of the cyanide level in the blood serum can arise very rapidly, even on short-term use of SNP, because of the over-dosage which then occurs. If in this case the tolerance limit of about 0.8 ug of CN/100 ml of blood plasma is exceeded, severe cyanide poisoning and even death can arise (see Anesthesiology 47, 441–448 (1977); Bull.

Med. Legale Toxicol. 21, 215–224 (1978); Amer. J. Obstet. Gynecol. 139, 708–711 (1981).

A further disadvantage of SNP is the appearance of the so-called "rebound" hypertension owing to persistent counter-regulation after termination of the SNP infusion. (New England J. Med. 302, 1029–1030 (1980); Anesthesiology 44, 345–348 (1976)). Since this "rebound" hypertension occasionally causes blood pressure levels which lie far above the initial blood pressure, secondary bleedings can occur in newly operated patients and dangerous blood perfusion disorders in the brain owing to oedema formation can occur in predisposed patients.

Since, on the other hand, SNP is at present the most active agent for the controlled lowering of blood pressure, e.g., during operations, attempts have been made to eliminate the mentioned disadvantages.

MacRae has recently proposed (Anaesthesia 36, 312-315 (1981)) to infuse a very dilute solution containing SNP together with the ganglionic blocking agent trimethaphan camsylate (TMC), in the weight ratio 1:10. He reported that thereby the amount of SNP required for the same lowering of the blood pressure was considerably lower.

TMC and its blood pressure-lowering activity are known and TMC is therefore employed therapeutically (in spite of its lower activity) similarly to SNP, i.e., as an infusion preparation for the controlled short-term lowering of blood pressure. However, TMC displays, in turn, a series of side effects which restrict its use.

Thus, in addition to such side effects as tachycardia, mydriasis, cycloplegia, urine retention, xerostomia and constipation, which occur by blockade of the parasympathetic ganglia, nausea or vomiting can arise in sensitive patients and, especially in children and aged patients, allergies can arise owing to histamine liberation.

Moreover, trimethaphan camsylate must not be used alone in the case of operations in the region of the gastrointestinal tract.

The dosage of SNP required for the controlled lowering of blood pressure is on average about 3 ug/kg body weight per minute, that of the TMC about 30 ug/kg or more per minute. Corresponding to this ratio of the pharmacological activities the concentrations of the infusion solutions usually used are thus 0.01 and 0.1%, respectively. According to Table 2 of MacRae (loc. cit.) a ratio of the dose rates of 1:14 and of the total dosage of 1:10 correspond to the relative strengths of the two agents.

According to MacRae, the clinical activities of the single components in dilute infusion solution containing SNP and TMC in the weight ratio of 1:10 appear to be additive or even become potentiated, while the corresponding sideeffects (because of their qualitative difference) are relatively diminished. Thus, seeing that ad hoc preparation of the dilute infusion solution containing such a mixture in the clinic is complicated and, because of the errors which are possible in practice, even dangerous, it appeared advantageous to develop appropriate combination products as well as concentrates thereof which are relatively stable and could easily be diluted to infusion strength.

An additional obstacle to the development of a combination product of nitroprusside and trimethapan was the fact that the two single drugs are not compatible in water and purely aqueous solvents concentrated form [see for example the solubilities given in Example 10]. When preparing an aqueous solution of the mixture either drug had firstly to be diluted to infusion strength, and these solutions could then be mixed shortly before the infusion. Because of the limited storage stability of dilute solutions of TMC and SNP and because of the known extreme light sensitivity of SNP solutions, such a highly diluted combination produce is, in any event, not suitable as a commercial product.

The observation that the hitherto unknown nitroprussides of short-acting ganglionic agents, such as sulfonium and ammonium bases, for example, pentolinium and tetraethylammonium and, especially, trimethaphan, can be isolated in pure form and in high yield and can be processed to a storable pharmaceutical composition was therefore suprising.

It was also unknown and unobvious that these salts can form solvates and concentrated aqueous alcoholic solutions, especially in view of their limited solubility in water.

It was also not obvious that mixtures of an alkali nitroprusside, such as sodium nitroprusside, and a water-soluble salt of such a short-acting ganglionic blocking agent as trimethaphan camsylate or a halogenide, e.g., the chloride or bromide, could be dissolved in aqueous ethanol and that such solutions, in addition, may contain other physiologically acceptable alcohols, such as polyols, like glycerol, inosotol, pentaereythol, mannitol, or isosorbitol as well as nitrates, like mono-, di-, tri- or tetranitrates thereof, especially nitroglycerin, preferably in an amount not exceeding the amount of nitroprusside to be dissolved, as well as nucleosides, such as inosine and adenosine, short-acting positive inotropic agents, such as dopamine or dobutamine, a physiologically acceptable thiosulfate, such as sodium thiosulfate or nicotinic acid and/or its biological precursors, like betapyridylcarbinol.

BRIEF DESCRIPTION OF THE INVENTION

In accordance with the present invention, there are provided novel complex salts (adducts) of nitroprusside and short-acting ganglionic blocking agents, such quaternary sulfonium or ammonium bases, for example, pentolinium, tetraethylammonium, or especially trimethaphan or its (+)isomer, solid compositions containing these, as well as concentrates thereof.

Particularly, in accordance with the present invention, there is provided the complex salt bis-(trimethaphan)-nitroprusside of formula:

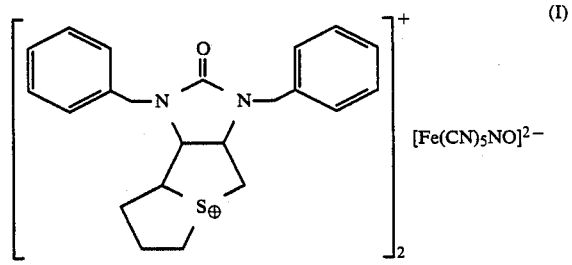

especially in the form of its (+)-isomer, which compounds are novel and possess interesting pharmacodynamic properties.

Also there are provided solid compositions (mixtures) of an alkali nitroprusside, especially sodium nitroprusside, and the soluble salt of a short-acting ganglionic agent, especially of trimethaphan or its (+)-isomer, in particular the camsylate or a halogenide, such as the chloride or bromide thereof, as well as concentrated solutions (stock solutions) containing said novel nitroprussides and compositions.

Furthermore, there are claimed pharmaceutical compositions which contain the novel active substance (I) in solid form, in form of concentrated solutions, or in form of diluted solutions suitable for infusion purposes.

Preferred mixtures claimed are those containing the nitroprusside and the salt of a ganglionic blocking agent, especially of trimethaphan or its (+)-isomer, in the weight ratio 1:<10, especially in a ratio representing the nitroprusside salt of the ganglionic blocking agent, e.g., bis-(trimethaphan)-nitroprusside. Also described are solutions, especially concentrated (stock) solutions of said nitroprussides and mixtures in physiologically acceptable alcohols, especially in aqeous ethanol.

Also claimed are the nitroprussides, especially bis-(trimethaphan)-nitroprusside, as well as its solvates, and said mixtures, especially those of an alkaline nitroprusside and a soluble trimethaphan salt, preferably in the weight ratio 1:<10, especially of about 1:4 when being dissolved in a physiologically acceptable alcohol, especially in aqueous ethanol, especially at least 40% or preferably about 60% ethanol.

Preferably, these nitroprussides and mixtures are stored in the solid form and dissolved in the alcohol immediately before use. In such a case, the alcohol may, in addition, contain other physiologically acceptable alcohols, such as polyols, like glycerol, inositol, pentaerythritol, mannitol, or isosorbitol as well as nitrates, like mono-, di-, tri or tetranitrates thereof, especially nitroglycerin, preferably in an amount not exceeding the amount of nitroprusside to be dissolved, as well as nucleosides, such as inosine and adenosine, short-acting positive inotropic agents, such as dopamine or dobutamine, a physiologically acceptable thiosulfate, such as sodium thiosulfate or nicotinic acid and/or its biological precursors, like betapyridylcarbinol. Such mixtures are also novel and constitute one aspect of the invention.

The invention also relates to solvates, particularly hydrates and alcoholates, of said novel nitroprussides, the manufacture of these compounds, pharmaceutical compositions containing such compounds and the manufacture of such compositions, as well as the use of such compounds and of such pharmaceutical compositions in the controlled lowering of blood pressure, in the achievement of peripheral vasodilation, in the elimination of arterial spasms and/or in the reduction of myocardial oxygen consumption and of the work load of the heart after heart attack.

DETAILED DESCRIPTION OF THE INVENTION

Figure 1:
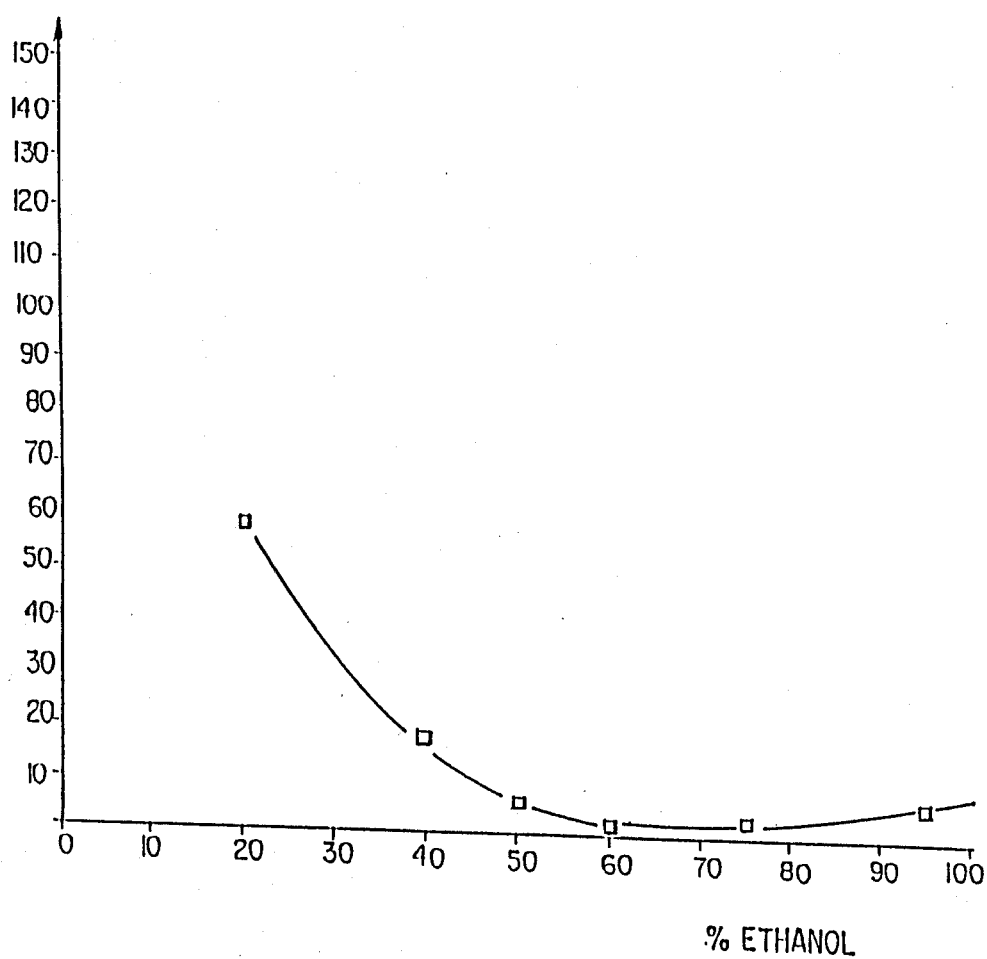
FIG. 1 shows the solution volumes for 50 mg. of I at room temperature in ethanol-water mixtures of various concentrations.

The compound of formula I, above, has the advantage that it is free from pharmacologically inactive material (sodium and camsylate ions), so that it has a considerably higher content of active material per weight unit: 1000 mg of the compound (I) in accordance with the invention contain the same amount of active material as 1575 mg of a mixture of 2 moles of TMC and 1 mole of SNP, which is also part of the invention. Such a reduction of the content of pharmaceutically inactive material can improve the tolerance of infusion preparations quite considerably.

Furthermore, the surprising and unforeseeable pharmacological finding was made that not a very dilute infusion solution of the mixture of equipotent amounts by weight (1:10) used by MacRae, but a solution containing nitroprusside and trimethaphan ions in the molar ratio (1:2) present in the compound of formula (I) gives the maximum synergistic activity. This is evident, for example, from the following experiment:

The various infusion solutions listed below were infused i.v. in succession, with appropriate recovery intervals, into a male, spontaneously respiring cat weighing 3.7 kg under Nembutal narcosis, and the dosages required to achieve a given lowering of the blood pressure were determined.

Substances and mixtures of substances tested

A—(+)-Bis-(trimethaphan)-nitroprusside
B—SNP (commerical product NIPRIDE)
C—TMC (commerical product ARFONAD)
D—The combination [mixture]of SNP and TMC [weight ratio 1:10, the ratio of SNP and TMC present in the infusion solution used by MacRae et al. - 125 mg of SNP plus 12.5 mg TMC in 500 ml of 5% dextrose solution]
E—The combination mixture of SNP and TMC (weight ratio 1:4)

For the preparation of the infusion solutions, the substances or their concentrated stock solutions were diluted with 0.9% sodium chloride solution to a uniform infusion strength of 9 mg/100 ml (90 ug/ml). All solutions were freshly prepared and infused with the exclusion of light (aluminium foil) corresponding to the dosages given below.

The values given in Table I hereinafter were determined graphically.

TABLE I

| Lowering of blood pressure (in mm Hg) | Infusion dosages (ug/kg · min) of the compounds A to E required to achieve a given lowering of the blood pressure | | | | |
|---|---|---|---|---|---|
| | Infusion dosage required for this effect in ug/kg · min | | | | |
| | A | B | C | D | E |
| −20 | 1.5 | 1.7 | 6.0 | 4.3 | 2.9 |
| −30 | 2.3 | 3.6 | 18 | 10 | 5.1 |
| −40 | 3.5 | 7.0 | 55 | 29 | 8.6 |
| −50 | 5.8 | 23 | * | 110 | 11.4 |
| −55 | 7.8 | 75 | * | * | 27 |
| −75 | 40 | * | * | * | * |

*Limit of activity and/or predominance of toxic side effects

From Table I the following conclusions can be drawn:

In the case of slight lowering of the blood pressure (to −30 mm Hg) A, B and E still have approximately comparable strengths of activity, although even in this range A surprisingly shows up best. In the case of greater lowerings of the blood pressure (and at the same time greater increases of the counter regulation not only B but also E distinctly fall off increasingly.

At about −55 mm Hg not only B but also E have reached the limit of their activity, i.e., with further increase in dosage only their toxic action increases.

C (TMC) is, as expected, significantly less active and reaches its limit of activity already at −40 mm Hg. D, the mixture of SNP and TMC (1:10) recommended by MacRae (1 oc. cit.), was also distinctly less active than SNP (B) alone. The limit of activity was in the case of D −50 mm Hg, however D was distinctly more active than C (TMC alone).

It was also surprising that A has a significantly higher limit of activity than all the other substances or mixtures.

Figure 4:
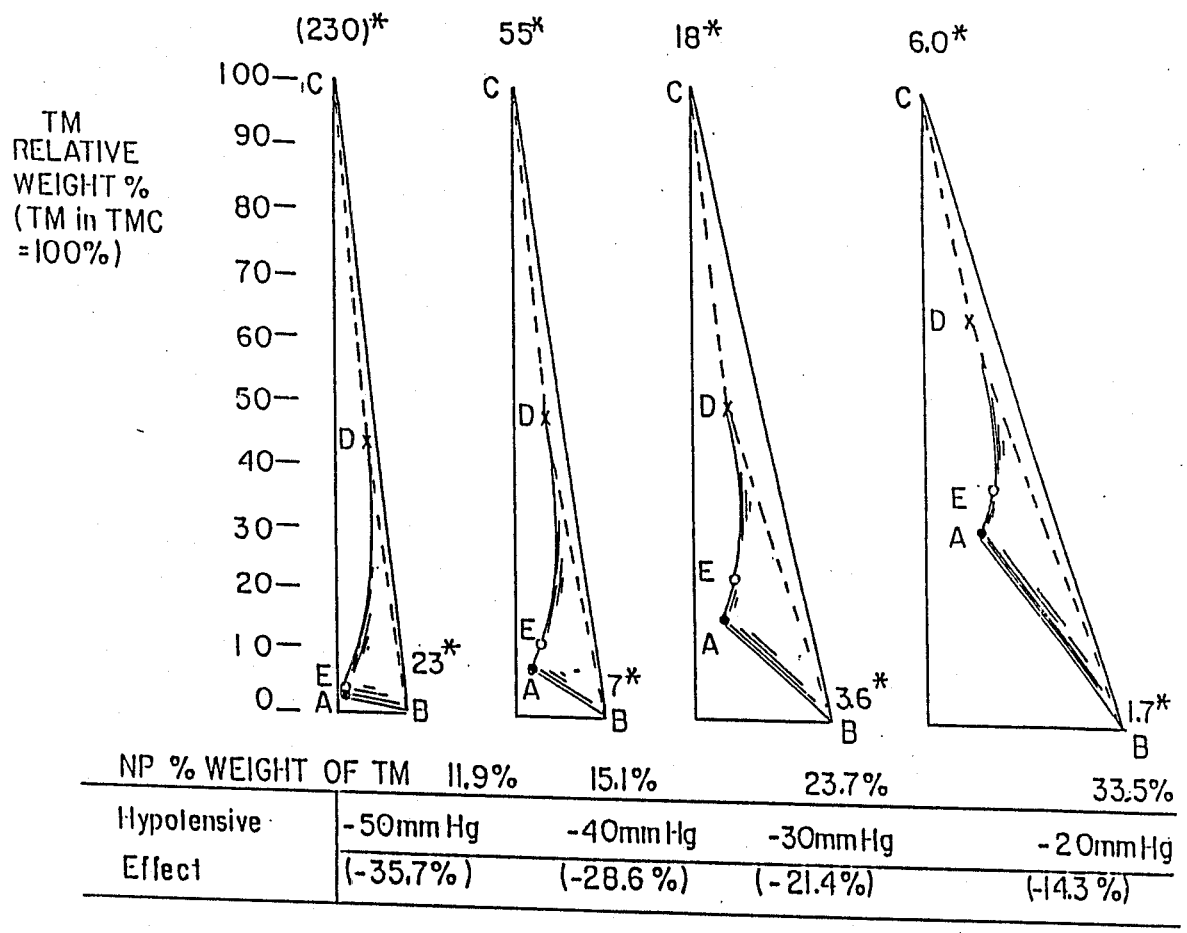
FIG. 4 shows a comparison of equieffective doses of (+)-bis-(trimethaphan)- nitroprusside, SNP, TMC, a combination of SNP and TMC in a weight ratio of 1:10; and a combination of SNP and TMC in a weight ratio of 1:4.

FIG. 4, a comparison of equieffective doses of A, B, C, D and E, is derived from the figures in Table I, and further indicates the unobvious superiority of infusion solutions having a weight ration of less than 1:10 of the salts.

On the Y-axis, the weight percent of the trimethaphan ion in trimethaphan camsylate needed to achieve the indicated level of hypotension reduction is always set at 100% for each level, indicating the infusion solution of C. The X-axis measures the weight of nitroprusside ion expressed as a weight percent of the trimethaphan ion needed; B, having no trimethaphan, is set at 0 weight percent. The percents for A, D, and E are as indicated.

The numbers with an asterisk are the absolute infusion rates of B and C taken from Table I of the application.

The hypotenuse of the triangle indicates the hypotensive effect expected to result from using mixtures of nitroprusside and trimethaphan ions. All values within the triangle demonstrate synergism. The lower and more to the left the values are, the higher the degree of synergism.

The dotted line shows the MacRAE ratio of 1:10, and the space between the dotted line and the hypotenuse indicates the synergism made obvious by MacRAE.

The shaded area indicates synergism not obvious from MacRAE.

FIG. 4 shows that as the level of blood pressure reduction increases, the area of the space between the dotted line and the hypotenuse decreases in comparison to the shaded area. Thus, as indicated by the tables shown previously, the graph demonstrates a trend of increasing discrepancy between the synergism of mixtures of less than 1:10 weight ratio, and the synergism of 1:10 mixtures. Thus, as was noted above, the invention relates to the use of the inventive composition in a weight ratio of less than 1:10, and preferably about 1:4. The invention thus includes the range of 1:4-<10. Within this range, narrower ranges of 1:9, 1:8, 1:7, 1:6, and 1:5 may be listed by way of example. It is clear, of course, that although integers are listed, intermediate ranges are also possible within the range set forth above.

Such data are unquestionable proof of the unobvious properties of the bis-(trimethaphan)-nitroprusside in isolated form, and of the nitroprusside and trimethaphan salts in the weight ratio of less than 1:10.

In accordance with the present invention, nitroprussides of short-acting ganglionic blocking agents, especially bis-(trimethaphan)-nitroprusside and solvates thereof can be prepared by reacting a solution of an alkali nitroprusside with a soluble salt of a short-acting ganglionic agent, such as pentolinium, tetramethylammonium or especially of a soluble trimethaphan salt, and, if desired, separating the less soluble product from the more readily soluble accompanying salts and isolating said product.

The reaction is conveniently carried out in a solvent containing the desired solvating agent, particularly in aqueous solution or in a solution which contains water and/or alcohol. In a preferred embodiment of the process of the invention, sodium nitroprusside and trimethaphan camsylate are brought together in aqueous solution, and the less soluble crystalline bis-(trimethaphan)-nitroprusside is isolated if desired.

The present invention is also concerned with pharmaceutical compositions which contain the novel active substance bis-(trimethaphan)-nitroprusside (I) in concentrated form or in dilute form suitable for infusion purposes, processes for their manufacture as well as their therapeutic use.

In a preferred embodiment of its composition aspect, the invention is concerned with a concentrated stock solution of I in at least 40% ethanol, which can also be prepared in situ from an appropriate amount of I (contained, for example, in a vial or a dry ampoule) and a small amount of at least 40% ethanol (contained, for example, in a sterile ampoule), whereby the ethanol is preferably 50 to 95, especially about 60%. The amount of solvent for the preparation of the stock solution preferably amounts to at most 20 ml, especially 2-5 ml.

A dilute (about 0.01%) infusion solution can be prepared from the concentrated stock solution at the place of use with a sterile conventional infusion liquid, such as 0.9% sodium chloride solution or 5% glucose solution. The dilute infusion solutions of the active substance I are also part of the invention.

The present invention also relates to solid compositions (mixtures) of an alkali nitroprusside, especially sodium nitroprusside, and a soluble salt of a short-acting ganglionic agent, especially of trimethaphan or its (+)-isomer, in particular the camsylate or a halogenide, such as the chloride or bromide thereof, as well as concentrated solutions (stock solutions) containing said novel nitroprussides and compositions.

Preferred mixtures are those containing the nitroprusside and the salt of a ganglionic blocking agent, especially of trimethaphan or its (+)-isomer, in the weight ratio 1:<10, especially in a ratio representing the nitroprusside salt of the ganglionic blocking agent, e.g., bis-(trimethaphan)-nitroprusside. Also described are solutions, especially concentrated stock solutions, of said nitroprussides and mixtures in physiologically acceptable alcohols, especially in aqueous ethanol.

Also claimed are the nitroprussides, especially bis-(trimethaphan)-nitroprusside, as well as its solvates, and said mixtures, especially those of an alkali nitroprusside and a soluble trimethaphan salt, preferably in the weight ratio of 1:<10, especially of about 1:4 when being dissolved in a physiologically acceptable alcohol, especially an aqueous ethanol, especially at least 40% or preferably about 60% ethanol.

Preferably, these nitroprussides and mixtures are stored in a solid form and dissolved in said alcohol immediately before use. In such a case, the alcohol may, in addition, contain other physiologically acceptable alcohols, such as polyols, like glycerol, inositol, pentaerythritol, mannitol, or isosorbitol, as well as nitrates, like mono-, di-, tri- or tetranitrates, thereof, especially nitroglycerin, preferably in an amount not exceeding the amount of nitroprusside to be dissolved, as well as nucleosides, such as inosine and adenosine, shortacting positive inotropic agents, such as dopamine or dobutamine, a physiologically acceptable thiosulfate, such as sodium thiosulfate, or nicotinic acid and/or its biological precursors, like beta-pyridylcarbinol. Such solutions are also part of this invention.

The mixture of I and thiosulphate should be present preferably at least in the weight ratio 1:1 and preferably at most in the weight ratio 1:40.

The pharmaceutical infusion solutions obtained from the above concentrates or solid mixtures according to the processes described below serve, for example, for the rapid and controlled lowering of blood pressure, for the peripheral vasodilation, for the elimination of arterial spasms and for the reduction of the myocardial oxygen consumption and of the work load of the heart after heart attack.

The compound I contains the nitroprusside anion which is also present in sodium nitroprusside.

In the case of the therapeutic administration of the novel compound I and of the mixtures and solutions described above, the danger of cyanide poisoning is considerably lower, since I contains a lower amount by weight of cyanide (13.7%) than SNP (43.6%) and, moreover, it can be administered at lower dosages than SNP. However, the latent danger of an accumulation of dangerous amounts of cyanide in the plasma still exists in particular circumstances (e.g., in patients with greatly reduced endogenous thiosulphate level or owing to exhaustion of the endogenous thiosulphate reserves in the case of long term application, high dosages or in the case of erroneous over-dosage). It is also known that higher plasma concentrations of cyanide ($>10^{-5}$ ug/ml) can greatly impair the vasodilatory activity of SNP (Amer. J. Physiol. 237, H 185–H190 (1979)). Therefore, high cyanide concentrations in the plasma are considered as being a factor responsible for the occurrence of tachyphylaxis during the therapeutic administration of SNP (Anesthesiology 51, 563–564 (1979)).

It is known that the toxicity of SNP can be reduced, e.g., in mice and rabbits, by simultaneous infusion of sodium thiosulphate (J. Pill, P. Engeser, M. Hobel, V.A.W. Kreye, Toxicology Letters, Suppl. 1, 156, p. 61 (1981)). These authors also proposed to use SNP and sodium thiosulphate in stoichiometric amounts (1:5 mol), i.e., to employ these agents in the weight ratio 1:4.16, whereby SNP is employed as the dihydrate (m.w. 298) and sodium thiosulphate is employed as the pentahydrate (m.w. 248.1).

The use of thiosulphate as a cyanide antidote has been known for a long time and is based on the fact that thiosulphate is the substrate of the enzyme rhodanase which converts cyanide into the not very toxic thiocyanate.

It therefore appears advantageous also to administer the compound I simultaneously with an amount of a water-soluble thiosulphate equivalent to the biologically liberated amount of cyanide.

In order to facilitate the control of the correct dosage for the physician, there comes into consideration for this purpose a uniform pharmaceutical composition (mixture) of I and thiosulphate, which, if desired, is already dissolved or can be brought into solution in a simple manner.

Suitable thiosulphates are in principle all physiologically acceptable thiosulphates which are soluble in water and in aqueous ethanol, such as alkali thiosulphates, e.g., potassium thiosulphate or sodium thiosulphate or its pentahydrate. However, sodium thiosulphate has to be given preference on practical reasons, because it is pharmacologically and clinically tested, has a very low toxicity (LD50 in rats, i.v., 2500 mg/kg) and is furthermore readily obtainable.

Corresponding to the amount of nitroprusside anion there can be formed from one mol of I (m.w.=947) 5 mol of cyanide, for the detoxification of which 5 mol of thiosulphate suffice in theory. The stoichiometric ratio (by weight) of I and sodium thiosulphate pentahydrate is thus 1:1.31 and the weight of sodium thiosulphate pentahydrate equivalent to the cyanide from 50 mg of I amounts to only 65.5 mg. This amount is thus significantly lower than the amount of sodium thiosulphate pentahydrate (208 mg) theoretically required for 50 mg of SNP.

Sodium thiosulphate is, however, used as a cyanide antidote (i.e., in the treatment of acute cyanide poisoning) in considerable excess, e.g., in dosages of 1 g up to 12.5 g, which have to be injected in aqueous solution and very slowly.

This excess is necessary in urgent cases of acute cyanide poisoning, since thiosulphate passes through biological membranes only very slowly and yet must be available rapidly and in large amount. However, the dosage can be reduced quite considerably in the case of prophylactic use. On the other hand, a certain excess is necesary, since thiosulphate is excreted relatively rapidly via the kidneys. It is therefore recommendable to use a multiple of the calculated stoichiometric thiosulphate dosage, e.g., up to 2000 mg per 50 mg of I (weight ratio 1:40).

For reasons of storage stability, medicaments intended for infusion are frequently marketed not as solutions, but in solid form. For obtaining an unobjectionable solution it is usual in such cases to prepare by means of a supplied solvent ampoule immediately prior to use a small amount of a concentrated solution and to dilute this to the infusion strength immediately.

It has been shown that thiosulphate is indeed suitable for the preparation of a pure by aqueous concentrated stock solution, but not the active substance I or a mixture thereof with thiosulphate:

FIG. 1 shows the solution volumes for 50 mg of I at room temperature (22° C.) in ethanol-water mixtures of various concentrations.

As is evident from FIG. 1, at least 40% ethanol is required for the preparation of a concentrated stock solution of I. On the other hand, sodium thiosulphate displayed only very limited solubility in over 40% ethanol, especially at temperatures <50° C. Mixtures of I and thiosulphate must not however, be heated in solution above 50° C., since otherwise the trimethaphan cation can decompose.

Therefore, the problem arose to find a physiologically acceptable solvent in which a mixture of I and thiosulphate in the weight ratio of about 1:1 to about 1:40 can dissolve to at least 5-10%, in a temperature range which for practical reasons should embrace temperatures between about 15° C. and about 35° C. Moreover, the concentrated solution should be able to dissolve without problem in the amount (250-1000 ml) of physiological sodium chloride solution or isotonic (5%) glucose solution required for final dilution.

Alternatively, a way was to be sought to enable the mixture of I and thiosulphate to be dissolved directly, rapidly and reliably in large volumes of the aforesaid infusion liquids with the avoidance of stock solutions.

It has now been found that 40-60% ethanol is suitable as a solvent for the preparation of concentrated stock solutions of mixtures of I and sodium thiosulphate up to a weight ratio 1:20 of the components.

For example, the mixture of 50 mg of I and 1000 mg of sodium thiosulphate pentahydrate dissolved at 37° C. in 10 ml
at 25° C. in 12 ml
at 20° C. in 13 ml and
at 15° C. in 15 ml of 55% ethanol.

Below the above-mentioned temperatures separation into two phases occurred immediately and thiosulphate crystallized out after a short time.

Figure 2:
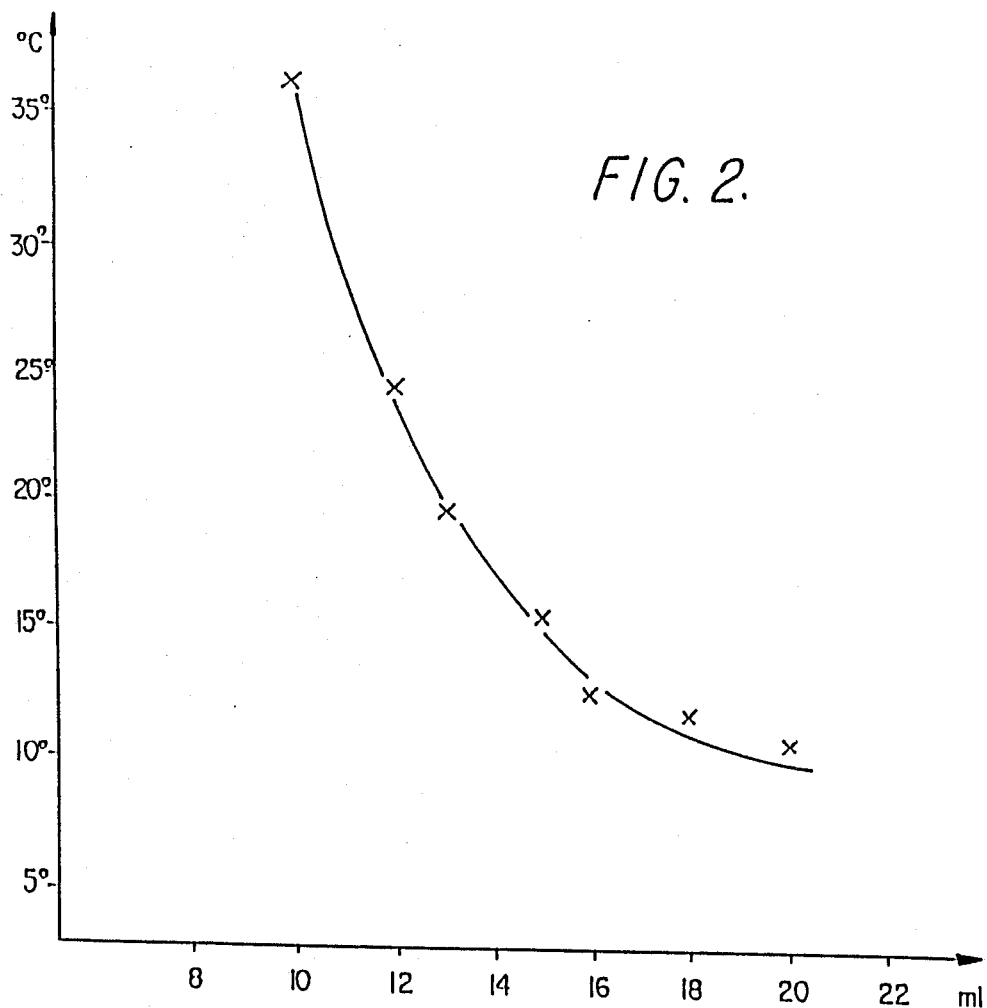
FIG. 2 shows the face phase separation temperature of a solution of 50 mg. of I and 1000 mg. of sodium thiosulfate pentahydrate in 55% ethanol as a function of the concentration.

FIG. 2 shows the phase separation temperature of a solution of 50 mg of I and 1000 mg of sodium thiosulphate pentahydrate in 55% ethanol as a function of the concentration.

In 50% ethanol the same mixture dissolved at 25° C. already in 8 ml. However, when it was cooled to temperatures below 22° C., phase separation occurred.

Thiosulphate has indeed a better solubility in weaker ethanol, but I is no longer completely soluble.

On the other hand, if the amount of thiosulphate in the mixture was reduced, then less or more concentrated ethanol (40-70%) could also be used for the preparation of a concentrated stock solution.

Figure 3:
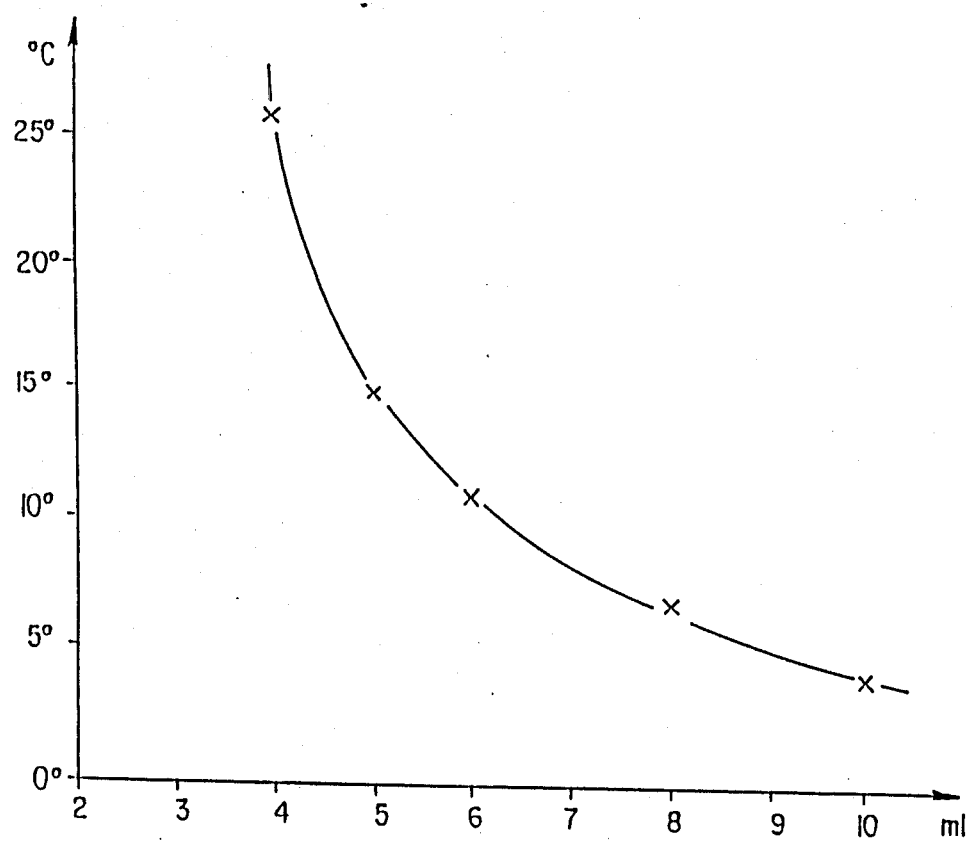
FIG. 3 shows the separation temperatures of a solution of 50 mg. of I and 500 mg. of sodium thiosulfate pentahydrate in 50% ethanol as a function of the concentration.

FIG. 3 shows the separation temperatures of a solution of 50 mg of I and 500 mg of sodium thiosulphate pentahydrate in 50% ethanol as a function of the concentration.

As FIG. 3 shows, a mixture in the weight ratio 1:10 (50+500 mg) already has a very good solubility in 50% ethanol: the latter mixture dissolved in accordance with FIG. 3 above 15° C. already in 5 ml of 50% ethanol.

The thus-obtained concentrated aqueous-alcoholic solutions dissolved without turbidity when poured into 220 ml of 0.9% sodium chloride solution or 5% glucose solution, thus their practical applicability is demonstrated.

The addition of a physiologically accepted alcohol is not a disadvantage. A small amount of ethanol does not interfere with the infusion, but rather brings about an additional slight vasodilatory effect, and is thus an acceptable solution to the problem described above.

If the amount of thiosulphate is increased to above 1000 mg per 50 mg of I, then a concentrated stock solution in above 40% ethanol-water mixtures can no longer be prepared at 15° C.

However, it has surprisingly been found that in this case a direct solution of the mixture in the given amount of 0.9% sodium chloride solution or 5% glucose solution is possible when it is used in finest pulverized form, at best in micronized form. It has been found that a micronized mixture of 50 mg of I and 2000 mg of sodium thiosulphate pentahydrate dissolves within a few seconds in 250 ml of 5% glucose solution, while a coarsely ground mixture dissolved only after shaking for more than 10 minutes.

The methods in accordance with the invention described above thus enable not only the compound I, which is poorly soluble in water, but also mixtures of I and thiosulphate to be converted in a reliable manner into corresponding infusion solutions.

Bis-(trimethaphan)-nitroprusside and the solid mixtures, as well as their alcoholic solutions needed to prepare the concentrated [stock], solutions described above, can be stored without further additives, when light is excluded and room temperature is not permanently exceeded.

The following Examples illustrate the present invention but are not intended to limit its extent. In these Examples all temperatures are given in degrees Centigrade.

EXAMPLE 1

29.8 g (0.1 mol) of sodium nitroprusside dihydrate are dissolved in 500 ml of water at room temperature. The reddish brown solution (solution A) obtained has to be protected from light.

119.4 g (0.2 mol) of (+)-trimethaphan camsylate are dissolved in 2000 ml of water and this solution, is placed in a 3.1 wide-necked vessel which is protected from light with aluminum foil. The solution A is added dropwise at room temperature with stirring and with occasional addition of seed crystals (or with occasional scratching). The velocity of the dropwise addition and the velocity of the stirring influence the size of the separating white to slightly yellowish crystals. The crystals are sucked off, rinsed several times with water and dried with the exclusion of light in vacuo at temperatures below 50°.

The compound thus obtained, (+)-bis-(trimethaphan)-nitroprusside, is only very slightly soluble in water, absolute ethanol and cyclohexane, but dissolves readily in aqueous ethanol.

If necessary, the compound can be recrystallized from aqueous ethanol or from methanol, optionally with addition of diethyl ether. On recrystallization from 70% ethanol there are obtained fine, yellowish-white needle clusters of melting point 200°−203° (decomposition).

The compound is solvated depending on the solvent used. Elemental analysis (after drying, 18 h at room temperature/$10^{-3}$ Torr over Siccapent):

| $C_{49}H_{50}O_3N_{10}S_2Fe$ Molecular weight 947.0 | | | | | |
|---|---|---|---|---|---|
| Calculated | C 62.15 | H 5.32 | N 14.79 | S 6.77 | $H_2O$ - (%) |
| Found | 61.75 | 5.48 | 14.83 | 6.89 | 0.65 (%) |

Systematic name: (+)-bis-/(3aS,8aR,8bR)-1,3-dibenzyl-decahydro-2-oxoimidazo[4,5-c]thieno[1,2-a]thiolium/-nitrosylpentacyano-ferrate.

The semihydrate forms compact needles from water (½ $H_2O$ calculated 0.94%, found 1.00%). It is stable at storage at room temperature and does not lose water under these conditions. Its solubility in water is 0.2% at room temperature. Its solubility in 60% ethanol is much better, and is about 3% at room temperature.

EXAMPEL 2

50 g of (+)-bis-(trimethaphan)-nitroprusside are dissolved at 25° in 2.8 l of 60% ethanol. The volume of the solution is brought to 3 l. After filtration over a Millipore filter, 3 ml portions of the solution are filled into sterile solvent ampoules manufactured from brown pyrogen-free glass.

The ampoules can even be stored at room temperature with exclusion of light. For the preparation of an infusion solution, the ampoule contents are dissolved in at least 220, at most 900 ml of sterile 0.9% sodium chloride solution or 5% glucose solution by vigorous shaking for a short time, whereafter the volume is brought to 250, 500 or 1000 ml. The infusion vessels and tubes are either to be covered with aluminum foil or must consist of material which is opaque to light.

The usual dosage amounts to 0.1-5 ug/kg.min, i.e., 0,5100 ul/kg.min. depending on the concentration used.

EXAMPLE 3

50 mg of finely pulverized (+)-bis-(trimethaphan)nitroprusside are filled into a sterilized, brown 5 ml flask closable with a synthetic stopper. 3 ml of 60% ethanol are sealed in a solvent ampoule and sterilized. Both substances can be stored for a very long time at room temperature and with exclusion of light. Immediately before use the solid substance is dissolved in the solvent and the thus-obtained stock solution is used for the preparation of the infusion solution.

EXAMPLE 4

A m icronized mixture of 50 mg of (+)-bis-(trimethaphan)-nitroprusside and 2000 mg of sodium thiosulphate pentahydrate is filled into a brown dry ampoule or a brown vial supplied with a lid and stored at room temperature with exclusion of light.

Immediately before use the mixture is added with vigorous stirring or shaking to a measuring flask with at least 220 ml, at most 900 ml of 0.9% sodium chloride solution or 5% glucose solution, whereafter the volume is brought to 250, 500 or 1000 ml.

EXAMPLE 5

A finely pulverized mixture of 50 mg of (+)-bis-(trimethaphan)-nitroprusside and 250 mg of sodium thiosulphate pentahydrate is filled into a brown 5 ml solvent ampoule and 5 ml of 55% ethanol are added thereto. After closing, the ampoules are stored with the exclusion of light.

EXAMPLE 6

A micronized mixture of 25 g of (+)-bis-(trimethaphan)-nitropruside and 125 g of sodium thiosulphate pentahydrate is dissolved in 2.5 l of 50% ethanol. The volume of the solution is brought to 3 l. After sterile filtration, 3 ml portions of the solution are filled into sterile, pyrogen-free brown solvent ampoules. The ampoules are sealed and stored with exclusion of light.

Immediately before use the contents of one ampoule are dissolved in at least 220 ml of 0.9% sodium chloride solution or 5% glucose solution and the volume is brought to 250, 500 or 1000 ml. The infusion solution is to be protected from the effect of light.

If the mid concentration were chosen (i.e., if the volume were brought to 500 ml), then the infusion dosage would amount in general to 2-100 ul/kg.min.

EXAMPLE 7

A brown solvent ampoule containing 50 mg of (+)-bis-(trimethaphan)-nitroprusside dissolved in 60% ethanol is packed together with a colourless solvent ampoule containing 250 mg of sodium thiosulphate dissolved in 3 ml of water. The ampoules are stored with exclusion of light.

Immediately before use the contents of the two ampoules are diluted with infusion liquid up to a volume of 250, 500 or 1000 ml. The obtained solution is to be protected from the effects of light.

EXAMPLE 8

25 mg of finely ground (+)-bis-(trimethaphan)-nitroprusside are mixed with 12.5 g of dry glucose. The mixture is ground again, if necessary, and then filled into a sterile PVC infusion bag or into a great dry ampoule.

For preparing an infusion solution from the dry ampoule, the contents of the dry ampoule are dissolved in 220 ml of water, whereafter the volume is brought to 250 ml.

For preparing an infusion solution in the infusion bag the contents of the infusion bag are dissolved by addition of 240 ml of water.

In both cases, the infusion solution contains (+)-bis-(trimethaphan)-nitroprusside in a concentration of 0.1 mg/ml (or 0.1 ug/ul) and 5% of glucose.

EXAMPLE 9

13.8 mg (52.8 umoles) of anhydrous sodium nitroprusside, 42.3 mg (105.6 umoles) of anhydrous (+)-trimethaphan chloride and 4.50 g of dry sodium chloride are mixed and finely ground with exclusion of light. The mixture is filled into a dry ampoule or into a PVC infusion bag.

For preparing an infusion solution from the dry ampoule, the contents of the dry ampoule are added, immediately before the infusion, to 450 ml of water "pro injectionem" with vigorous stirring or shaking in order to prevent the poorly soluble (+)-bis-(trimethaphan)-nitropruside which is formed in situ in finely divided form, from precipitating in the form of greater particles. Thereafter the volume is brought to 500 ml.

For preparing an infusion solution in the infusion bag, the appropriate amount of water (496 ml) is given into the bag and the contents of the bag are dissolved by shaking.

In both cases the infusion solution contains 0.9% of sodium chloride and (+)-bis-(trimethaphan)-nitroprusside in a concentration of 50 mg.liter (or 50 ug/ml or 0.05 ug/ul).

EXAMPLE 10

At room temperature (22° C.) clear solutions were obtained in the following solvents from the following compounds:

|  | Water | 5% Dextrose | 40% Ethanol | 60% Ethanol |
| --- | --- | --- | --- | --- |
| SNP (50 mg) | 2 ml | 2 ml | 2 ml | 3 ml |
| TMC (250 mg) | 10 ml | 10 ml | 10 ml | 2 ml |

When the concentrated solutions of SNP and TMC in water or in 5% dextrose are mixed directly, a milky suspension originates immediately from which a syrup separates which eventually crystallizes after a while.

This can only be brought in solution by stirring it in a very large excess of the aqueous solvent used (About 500 ml).

In the case of the 40% ethanol the deposit is smaller and much more readily soluble in water or dextrose solution. In the case of the 60% ethanol no deposit is formed at all, not even after cooling to 0° C.

| Solubility of Mixtures of SNP, TMC or of TNP | | | | |
| --- | --- | --- | --- | --- |
| | Water | 5% Dextrose | 40% Ethanol | 60% Ethanol |
| SNP + TNP (1 + 10) (50 + 500 mg) | 500 ml | 500 ml | 50 ml | 3 ml |
| SNP + TMC (1 + 4)$^{(0)}$ (125 + 500 mg) | — | 500 ml | — | 10 ml |
| TNP* (40 mg) | — | 100 ml$^{(x)}$ | 25 ml | 2 ml |

$^{(0)}$Preferred SNP/TMC mixture according to the invention
$^{(x)}$The solubility of a highly purified product is given here
*TNP (40 mg) has the same contents of the active ions (9.0 mg nitroprusside and 30.6 mg trimetaphan) as a mixture of 12.5 mg SNP and 50 mg TMC (weight ratio 1:4) which contains 9.06 mg. nitroprusside and 30.6 mg trimetapan ions.

The amounts of solvents given are borderline amounts which could not significantly be reduced without beginning precipitation of syrups or crystals.

EXAMPLE 11

12.5 mg of finely ground sterile sodium nitroprusside dihydrate and 100 mg sterile trimethaphan camsylate are mixed and filled into a 10 ml vial closed with a caoutchouc stopper. An ampoule containing 3 ml sterile 60% ethanol was co-packed. After storage at or below 20° C., just before use, the contents of the ampoule is injected under sterile conditions through the caoutchouc stopper, the mixture dissolved by shaking, the resulting clear solution again taken up by means of an injection syringe and injected into 500 ml of 5% dextrose in water solution contained in a sterile infusion bag.

The infusion rate should be 0.4 to 10 ul/kg. min according to the age of the patient and the degree of hypotension intended.

EXAMPLE 12

12.5 mg of hydrophilyzed sterile SNP and 50 mg of sterile TMC are mixed thoroughly and filled into a 10 ml vial, which can be treated as in Ex. 11.

EXAMPLE 13

12.5 mg of finely powdered SNP and 40 mg racemic Trimethaphan bromide are mixed and filled into a 10 ml vial and then treated as described in Ex. 11.

EXAMPLE 14

50 mg of SNP dihydrate and 55 mg Tetraethylammonium chloride are mixed and dissolved in 20 ml of 40% ethanol and then injected into 500 ml of sterile 0.9% (physiological) sodium chloride solution and infused at a rate of 2 to 15 ug/kg.min.

EXAMPLE 15

To 30 mg of finely ground SNP dihydrate and 54 mg pentolinium hydrogen tartrate were added 10 ml of 95% ethanol, the suspension refluxed for 20 minutes with exclusion of light and sucked off.

When the ethanolic filtrate was evaporated, ivory colored crystals of pentolinium nitroprusside separated.

EXAMPLE 16

40 mg of bis-(trimethaphan)-nitroprusside semihydrate were dissolved in 5 ml 60% ethanol, containing
(a) 40 mg nitroglycerin
(b) 40 mg nitroglycerin and 1000 mg glycerol, or
(c) 300 mg beta-pyridylcarbinol.

In any of these cases a clear solution resulted which could be diluted to infusion strength with 500 ml of 5% dextrose in water infusion liquid.

Although the Examples have been given only to weight ratios of 1:4 and 1:8, it is clearly understood, from Graph I, that synergistically improved results are obtained in all concentrations of less than 1:10.

Although the invention has been described with respect to particular means, materials and embodiments, it is to be understood that the invention is not limited to the particulars disclosed, and extends to all equivalents falling within the scope of the claims.

What is claimed is:

1. A nitroprusside of a short acting ganglionic blocking agent selected from the group consisting of sulfonium salts and ammonium salts.

2. A solvate of the nitroprusside of claim 1 wherein the solvate is derived from a physiologically acceptable solvent.

3. The nitroprusside of claim 1 which is tetraethylammonium nitroprusside.

4. The nitroprusside of claim 1 which is pentrolinium nitroprusside.

* * * * *